United States Patent
Yum (10) Patent No.: US 11,443,607 B2
(45) Date of Patent: *Sep. 13, 2022

(54) DUAL MODE BABY MONITORING

(71) Applicant: Binatone Electronics International Limited, Sheung Wan (HK)

(72) Inventor: Kenji Yum, Sheung Wan (HK)

(73) Assignee: Binatone Electronics International Limited, Sheung Wan (HK)

(*) Notice: Subject to any disclaimer, the term of this patent is extended or adjusted under 35 U.S.C. 154(b) by 0 days.

This patent is subject to a terminal disclaimer.

(21) Appl. No.: 16/988,468

(22) Filed: Aug. 7, 2020

(65) Prior Publication Data

US 2020/0372777 A1 Nov. 26, 2020

Related U.S. Application Data

(63) Continuation of application No. 15/109,797, filed as application No. PCT/CN2015/070178 on Jan. 6, 2015, now Pat. No. 10,741,041.

(Continued)

(51) Int. Cl.
*G08B 21/02* (2006.01)
*H04L 69/18* (2022.01)
(Continued)

(52) U.S. Cl.
CPC ......... *G08B 21/0208* (2013.01); *G08B 21/02* (2013.01); *G08B 21/182* (2013.01);
(Continued)

(58) Field of Classification Search
CPC G08B 21/00; G08B 21/0202; G08B 21/0208; G08B 21/0227; G08B 21/02; G08B 21/0288
See application file for complete search history.

(56) References Cited

U.S. PATENT DOCUMENTS 5,640,147 A * 6/1997 Chek .................. G08B 21/0208
340/573.4
H1713 H * 3/1998 Pearlman ...................... 340/531
(Continued)

FOREIGN PATENT DOCUMENTS

CN 102103786 A 6/2011
CN 202421817 U 9/2012
(Continued)

OTHER PUBLICATIONS

European Office Action dated Jan. 21, 2020 for European Application No. 15733112.5, a counterpart of U.S. Appl. No. 15/109,797, 3 pages.
(Continued)

*Primary Examiner* — Curtis J King
(74) *Attorney, Agent, or Firm* — Lee & Hayes, P.C.

(57) ABSTRACT

The techniques and systems described herein determine whether a computing device is within a particular range to communicate with a monitoring device. If the computing device is within the particular range, the computing device is configured to communicate with the monitoring device via a primary monitoring communication mode (e.g., a radio frequency RF channel). If the computing device is outside the particular range, the computing device is configured to communicate with the monitoring device via a secondary monitoring communication mode (e.g., a Wi-Fi channel or a mobile telephone network MTN channel). The computing device receives, from the monitoring device via the primary monitoring communication mode or the secondary monitoring communication mode, monitoring information associated with a monitored subject (e.g., a baby) or associated with an area in which the monitored subject is located (e.g., a room of a residential dwelling).

20 Claims, 4 Drawing Sheets

Related U.S. Application Data (60) Provisional application No. 61/924,172, filed on Jan. 6, 2014.

(51) Int. Cl.
    *G08B 25/08*   (2006.01)
    *G08B 21/18*   (2006.01)
    *H04L 67/125*  (2022.01)
    *H04W 4/80*    (2018.01)
    *G16H 40/67*   (2018.01)
    *H04B 17/318*  (2015.01)
    *H04W 4/02*    (2018.01)
    *H04W 84/04*   (2009.01)
    *H04W 84/12*   (2009.01)

(52) U.S. Cl.
    CPC ............ *G08B 25/08* (2013.01); *G16H 40/67* (2018.01); *H04B 17/318* (2015.01); *H04L 67/125* (2013.01); *H04L 69/18* (2013.01); *H04W 4/80* (2018.02); *H04W 4/023* (2013.01); *H04W 84/042* (2013.01); *H04W 84/12* (2013.01)

(56) References Cited

U.S. PATENT DOCUMENTS

| | | | |
|---|---|---|---|
| 6,216,158 B1 | 4/2001 | Luo et al. | |
| 7,136,999 B1* | 11/2006 | Griffiths | H04L 63/0492 713/168 |
| 7,138,921 B1* | 11/2006 | Fontaine | G08B 13/196 340/573.4 |
| 7,151,764 B1* | 12/2006 | Heinonen | H04W 48/08 370/338 |
| 7,272,232 B1 | 9/2007 | Donaldson et al. | |
| 7,349,782 B2* | 3/2008 | Churchill | G08G 1/164 340/438 |
| 7,428,449 B2* | 9/2008 | Fehr | B60W 40/08 701/1 |
| 7,454,041 B2* | 11/2008 | Sukegawa | G06K 9/00288 382/118 |
| 7,679,507 B2 | 3/2010 | Babich et al. | |
| 8,094,013 B1 | 1/2012 | Lee et al. | |
| 8,542,087 B1 | 9/2013 | Spector | |
| 8,707,201 B1* | 4/2014 | Aradhye | H04L 51/26 715/789 |
| 8,825,871 B2* | 9/2014 | Baum | G08B 25/003 709/227 |
| 8,954,517 B2* | 2/2015 | Yoakum | H04M 3/53341 709/206 |
| 9,282,587 B2* | 3/2016 | Winkler | H04M 1/72454 |
| 9,464,517 B2* | 10/2016 | Papouras | E21B 47/00 |
| 9,740,187 B2* | 8/2017 | Lobb | G06K 9/00335 |
| 9,817,869 B2 | 11/2017 | Aradhye et al. | |
| 2003/0048222 A1* | 3/2003 | Schmid | H01Q 3/267 342/359 |
| 2003/0137419 A1* | 7/2003 | Gehlot | G08B 21/028 340/572.1 |
| 2003/0156027 A1* | 8/2003 | Seo | G08B 13/191 340/523 |
| 2004/0135879 A1 | 7/2004 | Stacy et al. | |
| 2005/0099294 A1* | 5/2005 | Bogner | G16H 40/63 340/540 |
| 2005/0245839 A1* | 11/2005 | Stivoric | A61B 5/0008 600/549 |
| 2005/0273700 A1* | 12/2005 | Champion | G06F 3/04883 715/233 |
| 2005/0280704 A1* | 12/2005 | Clare | H04N 7/181 348/143 |
| 2006/0009863 A1* | 1/2006 | Lingemann | G05B 15/02 700/19 |
| 2006/0248554 A1 | 11/2006 | Priddy | |
| 2007/0135866 A1* | 6/2007 | Baker | H04L 67/28 607/60 |
| 2007/0155375 A1* | 7/2007 | Kappel | H04W 24/04 455/422.1 |
| 2007/0210909 A1* | 9/2007 | Addy | H04L 63/1458 340/506 |
| 2007/0241911 A1 | 10/2007 | Swan et al. | |
| 2007/0285259 A1 | 12/2007 | Desrosiers et al. | |
| 2007/0285570 A1 | 12/2007 | Desrosiers et al. | |
| 2007/0287394 A1 | 12/2007 | Swan et al. | |
| 2007/0290841 A1* | 12/2007 | Gross | G08C 17/00 340/539.13 |
| 2008/0068157 A1* | 3/2008 | Ikemori | G08B 21/0269 340/539.23 |
| 2008/0074256 A1* | 3/2008 | Hirai | G08B 21/22 340/541 |
| 2008/0275312 A1* | 11/2008 | Mosesov | A61B 5/0031 600/300 |
| 2008/0275701 A1* | 11/2008 | Wu | G06F 16/685 704/235 |
| 2008/0284580 A1* | 11/2008 | Babich | G08B 13/19697 340/502 |
| 2008/0309765 A1 | 12/2008 | Dayan et al. | |
| 2009/0195655 A1* | 8/2009 | Pandey | G08B 13/19647 348/158 |
| 2009/0201201 A1* | 8/2009 | Foster | G08G 1/0962 342/357.75 |
| 2009/0207014 A1* | 8/2009 | Ayed | G08B 13/1427 340/539.13 |
| 2009/0221261 A1* | 9/2009 | Soliman | H04W 88/04 455/343.2 |
| 2010/0081895 A1 | 4/2010 | Zand | |
| 2010/0109878 A1 | 5/2010 | Desrosiers | |
| 2010/0121157 A1* | 5/2010 | Espina | A61B 5/002 600/301 |
| 2010/0159948 A1* | 6/2010 | Spivey | H04L 12/10 455/456.1 |
| 2010/0195810 A1* | 8/2010 | Mota | H04N 7/186 379/167.12 |
| 2010/0241018 A1 | 9/2010 | Vogel | |
| 2010/0245087 A1* | 9/2010 | Gerner | G07C 9/28 340/541 |
| 2010/0315230 A1* | 12/2010 | Kwon | G08B 25/10 340/540 |
| 2011/0227756 A1* | 9/2011 | Otero | G08G 1/096716 340/901 |
| 2011/0267462 A1 | 11/2011 | Cheng et al. | |
| 2011/0317007 A1* | 12/2011 | Kim | G08B 17/10 348/143 |
| 2012/0032797 A1 | 2/2012 | Babineau | |
| 2012/0069827 A1* | 3/2012 | Lee | H04W 52/0274 370/338 |
| 2012/0072751 A1* | 3/2012 | Das | H04W 76/45 713/323 |
| 2012/0105229 A1* | 5/2012 | Kates | G08B 13/19697 340/541 |
| 2012/0119921 A1* | 5/2012 | Farley | G08B 27/005 709/206 |
| 2012/0120858 A1* | 5/2012 | Das | H04W 52/0229 370/311 |
| 2012/0164968 A1* | 6/2012 | Velusamy | H04W 4/027 455/404.2 |
| 2012/0172088 A1* | 7/2012 | Kirch | G06F 1/1626 455/557 |
| 2012/0268267 A1* | 10/2012 | Anderson | B60R 25/1004 340/539.1 |
| 2012/0327229 A1* | 12/2012 | Poder | G08B 25/002 348/143 |
| 2013/0107029 A1 | 5/2013 | Knasel et al. | |
| 2013/0169735 A1 | 7/2013 | Barker et al. | |
| 2013/0250080 A1* | 9/2013 | Farrell | G08B 21/0283 348/77 |
| 2013/0297330 A1* | 11/2013 | Kamen | G16H 20/40 705/2 |
| 2014/0062706 A1* | 3/2014 | Frazier | G08B 21/18 340/632 |

(56) References Cited

U.S. PATENT DOCUMENTS

| | | | |
|---|---|---|---|
| 2014/0132416 A1* | 5/2014 | Hansson | G01N 33/004 340/632 |
| 2014/0155118 A1* | 6/2014 | Tsuda | H04W 52/38 455/522 |
| 2014/0184408 A1* | 7/2014 | Herbst | G08B 27/006 340/539.12 |
| 2014/0192135 A1 | 7/2014 | Babineau et al. | |
| 2014/0230755 A1* | 8/2014 | Trenkle | G01C 21/367 119/859 |
| 2014/0232541 A1* | 8/2014 | Trenkle | G08B 25/10 340/539.13 |
| 2014/0253708 A1* | 9/2014 | Allen | G08B 13/14 348/77 |
| 2015/0009029 A1 | 1/2015 | Martin | |
| 2015/0022355 A1* | 1/2015 | Pham | G08B 25/10 340/541 |
| 2015/0038072 A1 | 2/2015 | Cordier et al. | |
| 2015/0045634 A1* | 2/2015 | Goldberg | A61B 5/681 600/301 |
| 2015/0061866 A1 | 3/2015 | Lee et al. | |
| 2015/0091722 A1 | 4/2015 | Poder | |
| 2015/0094544 A1* | 4/2015 | Spolin | A61B 5/6831 600/301 |
| 2015/0133747 A1 | 5/2015 | Spolin et al. | |
| 2015/0157263 A1* | 6/2015 | Workman | G16H 40/67 600/324 |
| 2015/0161836 A1* | 6/2015 | Park | B60R 25/2045 340/5.51 |
| 2015/0207796 A1* | 7/2015 | Love | A61B 5/1495 600/345 |
| 2015/0282061 A1* | 10/2015 | Matthews | H04W 4/90 455/404.2 |
| 2016/0035205 A1* | 2/2016 | Messenger | G08B 21/0492 340/539.15 |
| 2016/0037482 A1* | 2/2016 | Higgins | H04W 4/027 455/414.1 |
| 2016/0071389 A1* | 3/2016 | Sun | G08B 21/0208 340/539.15 |
| 2016/0284176 A1* | 9/2016 | Harrington | F21V 23/04 |
| 2016/0335870 A1 | 11/2016 | Yum | |
| 2017/0039834 A1* | 2/2017 | Moller | G08B 21/0238 |
| 2018/0047279 A1* | 2/2018 | Probin | G08B 25/008 |
| 2018/0098206 A1* | 4/2018 | Nguyen | H04L 51/32 |
| 2018/0156667 A1* | 6/2018 | Chrostowski | G01J 5/025 |
| 2021/0375157 A1* | 12/2021 | Sundstrom | G06Q 30/018 |

FOREIGN PATENT DOCUMENTS

| | | |
|---|---|---|
| CN | 102855733 A | 1/2013 |
| CN | 103237292 A | 8/2013 |
| GB | 2396043 A | 6/2004 |
| WO | WO2004109992 A1 | 12/2001 |
| WO | WO2004109992 A1 | 12/2004 |
| WO | WO2015017367 A1 | 2/2015 |

OTHER PUBLICATIONS

European Office Action dated Oct. 1, 2018 for European Application No. 15733112.5, a counterpart foreign patent application of the U.S. Appl. No. 15/109,797, 4 pages.

Extended European Search Report dated Oct. 17, 2017 for European Patent Application No. 15733112.5, 11 pages.

Partial Supplementary European Search Report dated Jul. 14, 2017 for European Patent Application No. 15733112.5, 11 pages.

Office Action for U.S. Appl. No. 15/109,797, dated Jan. 24, 2019, Yum, "Dual Mode Baby Monitoring", 14 pages.

Office Action for U.S. Appl. No. 15/109,797, dated Jan. 25, 2018, Yum, "Dual Mode Baby Monitoring", 13 pages.

Office Action for U.S. Appl. No. 15/109,797, dated Jun. 15, 2018, Yum, "Dual Mode Baby Monitoring", 15 pages.

Office Action for U.S. Appl. No. 15/109,797, dated Jul. 26, 2017, Yum, "Dual Mode Baby Monitoring", 13 pages.

Office Action for U.S. Appl. No. 15/109,797, dated Aug. 7, 2019, Yum, "Dual Mode Baby Monitoring", 13 pages.

PCT Search Report and Written Opinion dated Apr. 15, 2015 for PCT application No. PCT/CN2015/070178, 13 pages.

European Office Action dated Oct. 1, 2018 for European Patent Application No. 15733112.5, a counterpart of U.S. Appl. No. 15/109,797, 4 pages.

Extended European Search Report dated Oct. 17, 2017 for Europears Patent Application No. 15733112.5, 11 pages.

Partial Supplementary European Search Report dated Jul. 14, 2017 for European Application No. 15733112.5, 11 pages.

European Office Action dated Jul. 30, 2021 for European Application No. 15733112.5, a counterpart of U.S. Appl. No. 15/109,797, 4 pages.

* cited by examiner

DUAL MODE BABY MONITORING

PRIORITY APPLICATION

This Application is a continuation of Ser. No. 15/109,797, filed, Jul. 5, 2016, which is a 35 U.S.C. § 371 National Stage Entry of and claims priority from PCT Application Serial No. PCT/CN2015/070178, titled "Dual Mode Baby Monitoring", filed on Jan. 6, 2015, which claims priority from U.S. Provisional Application No. 61/924,172, filed Jan. 6, 2014, and entitled "Dual Mode Baby Monitoring," the entirety of which are incorporated herein.

BACKGROUND

Conventional baby monitoring techniques typically use a device that is dedicated to baby monitoring and that is unable to perform other functionality (e.g., web browsing, receiving emails, gaming, etc.). In many instances, a personal device (e.g., a smartphone, a tablet, etc.) of a parent is unable to be used to reliably and efficiently receive baby monitoring information.

SUMMARY

The techniques and systems described herein determine whether a computing device is within a particular range to communicate with a monitoring device. If the computing device is within the particular range, the computing device is configured to communicate with the monitoring device via a primary monitoring communication mode (e.g., a radio frequency RF channel). If the computing device is outside the particular range, the computing device is configured to communicate with the monitoring device via a secondary monitoring communication mode (e.g., a Wi-Fi channel or a mobile telephone network MTN channel). The computing device receives, from the monitoring device via the primary monitoring communication mode or the secondary monitoring communication mode, monitoring information associated with a monitored subject (e.g., a baby) or associated with an area in which the monitored subject is located (e.g., a room of a residential dwelling).

In various examples, the computing device may receive a notification from the monitoring device, the notification being associated with the monitoring device detecting a threshold amount of monitoring information (e.g., a threshold amount of motion, a threshold amount of noise, etc.). In response to receiving the notification, the computing device may prioritize the output of at least part of the monitoring information over other information currently being output at the computing device.

BRIEF DESCRIPTION OF THE DRAWINGS

The detailed description is set forth with reference to the accompanying figures. In the figures, the left-most digit(s) of a reference number identifies the figure in which the reference number first appears.

DETAILED DESCRIPTION

This disclosure describes techniques and systems configured to operate devices in dual monitoring communication modes for purposes of monitoring a baby. While the embodiments and examples provided herein are discussed with respect to a baby, they may also be applied to monitoring a toddler, a grandparent, a patient, or another individual to be monitored. In various embodiments, the systems include a monitoring device configured to monitor the baby in a particular area. For example, the particular area may include, but is not limited to, a crib (e.g., when the baby is sleeping or should be sleeping), a baby room, a play area (e.g., when the baby is playing with toys), etc. The systems may also include a computing device configured to communicate with the monitoring device in at least two different monitoring communication modes (e.g., dual monitoring communication modes). A communication mode may be one of a variety of communication channels or protocols. The computing device may be used by a monitoring person (e.g., a parent of the baby) to receive monitoring information from the monitoring device.

In various embodiments, the computing device may also be configured to simultaneously perform other functionality in addition to continually receiving monitoring information. For example, the computing device may be configured to perform web browsing, online gaming, video streaming, etc. Thus, the computing device described herein may be a device optimized for, or dedicated to, monitoring a baby, but the computing device may also provide a parent with the convenience of executing other functionality. In various embodiments, the computing device may be configured (e.g., pre-loaded) with a variety of applications designed for parenting. Accordingly, the computing device described herein provides reliable monitoring while also allowing a parent to use the computing device to perform other functionality configured on the computing device.

Figure 1:
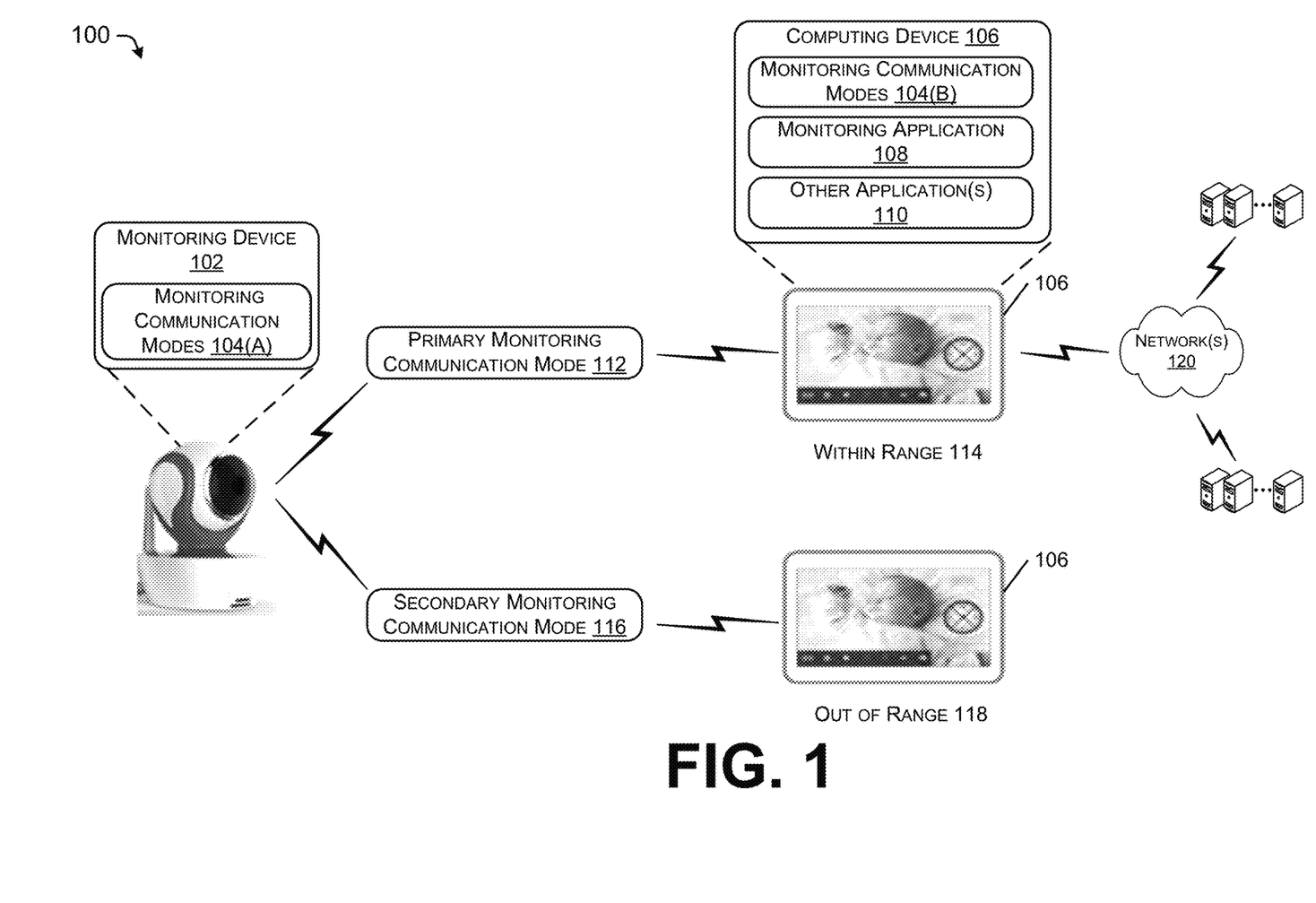
FIG. 1 is a diagram showing an example environment that implements the monitoring techniques and systems discussed herein.

FIG. 1 is a diagram showing an example environment 100 that implements the techniques and systems discussed herein, in accordance with various embodiments. The environment 100 includes a monitoring device 102 configured to operate in at least two possible monitoring communication modes 104(A). In various embodiments, the monitoring device 102 operates in a single monitoring communication mode at a given time. For instance, the monitoring device 102 may be configured to communicate with a computing device 106 via one or both of the monitoring communication modes 104(A). Correspondingly, the computing device 106 is also configured to operate in at least two possible monitoring communication modes 104(B). The computing device may also be configured to operate a monitoring application 108 and other application(s) 110 (e.g., baby apps, gaming apps, social media apps, browsing apps, e-reading apps, etc.), as further discussed herein. In various embodiments, the monitoring device 102 and the computing device 106 each operate in one of the two possible communication modes at a given time.

As illustrated in FIG. 1, the monitoring device 102 and the computing device 106 may communicate (e.g., receive and/or transmit information to one another) in a primary monitoring communication mode 112 (e.g., communication link, communication channel, etc.) if the computing device 106 is within a particular communication range 114 of the monitoring device 102. For example, the monitoring device 102 and the computing device 106 may communicate via the primary monitoring communication mode 112 when the monitoring device 102 is in a room of a house where the baby is sleeping and the computing device 106 is in a separate room of the same house where a parent of the baby is web browsing via the computing device 106 (e.g., the living room or the parent's bedroom). Further, the monitoring device 102 and the computing device 106 may communicate in a secondary monitoring communication mode 116 if the computing device 106 is outside the particular communication range 118 of the monitoring device 102. For example, the monitoring device 102 and the computing device 106 may communicate via the secondary monitoring communication mode 116 when the monitoring device 102 is in a room of a house where the baby is sleeping and the computing device 106 is with a parent who is across the street talking to a neighbor.

In various embodiments, the computing device 106 may comprise, but is not limited to, any one of a variety of devices, such as a smartphone, a tablet computer, a mobile phone, a personal digital assistant (PDA), an electronic book device, a laptop computer, a desktop computer, a portable computer, a gaming console, a personal media player device, a server computer or any other electronic device that may be configured or receive monitoring information from the monitoring device 102 for purposes of baby monitoring.

Therefore, the computing device 106 includes one or more processors and memory. In various embodiments, the memory includes an operating system (e.g., Android®, Windows®, iOS®) that is configured to manage hardware and services within and coupled to a device for the benefit of other modules, components and devices. The processor(s) may be a single processing unit or a number of units, each of which could include multiple different processing units. The processor(s) may include a microprocessor, a microcomputer, a microcontroller, a digital signal processor, a central processing unit (CPU), a graphics processing unit (GPU), a security processor etc. Alternatively, or in addition, some or all of the techniques described herein can be performed, at least in part, by one or more hardware logic components. For example, and without limitation, illustrative types of hardware logic components that can be used include a Field-Programmable Gate Array (FPGA), an Application-Specific Integrated Circuit (ASIC), an Application-Specific Standard Products (ASSP), a state machine, a Complex Programmable Logic Device (CPLD), other logic circuitry, a system on chip (SoC), and/or any other devices that perform operations based on instructions. Among other capabilities, the processor(s) may be configured to fetch and execute computer-readable instructions stored in the memory.

The memory may include one or a combination of computer-readable media. As used herein, "computer-readable media" includes computer storage media and communication media. Computer storage media includes volatile and non-volatile, removable and non-removable media implemented in any method or technology for storage of information, such as computer-readable instructions, data structures, program modules, or other data. Computer storage media includes, but is not limited to, phase change memory (PRAM), static random-access memory (SRAM), dynamic random-access memory (DRAM), other types of random access memory (RAM), read only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium that can be used to store information for access by a computing device. In contrast, communication media includes computer-readable instructions, data structures, program modules, or other data in a modulated data signal, such as a carrier wave. As defined herein, computer storage media does not include communication media.

In various embodiments, the monitoring device 102 is configured to receive information from one or more sensors, process and/or store the information, and transmit the information to the computing device 106. For example, the monitoring device 102 may comprise, or in some way be coupled to, a camera (e.g., with one or more imaging sensors) that can capture imagery (e.g., video) of the baby and/or still images of the baby. In another example, the monitoring device 102 may comprise, or in some way be coupled to, temperature sensors configured to measure and communicate a temperature of the area in which the baby is located. In yet another example, the monitoring device 102 may comprise, or in some way be coupled to, noise or audio sensors (e.g., a microphone) configured to determine when the baby is making noise (e.g., a baby is crying).

In various embodiments, the monitoring device 102 is configured with logic to process and store information received from the sensors. The logic may also be configured to process information received from the computing device 106 (e.g., a parent's voice, a download of a particular song). The monitoring device 102 may output audio via one or more speakers. Accordingly, the monitoring device 102 may also include one or more processors and memory as discussed above with respect to the computing device 106.

In various embodiments, the primary monitoring communication mode 112 is a dedicated communication channel or communication link for monitoring. In some instances, the primary monitoring communication mode 112 is configured to provide one or more of higher quality monitoring information (e.g., high definition video of a baby sleeping), interference-free communication, and greater reliability compared to the secondary monitoring communication mode 116. For example, the primary monitoring communication mode 112 may comprise a radio frequency (RF) communication channel or communication link (e.g., a 2.4 GHz wireless technology). The secondary monitoring communication mode 116 may comprise a Wi-Fi communication channel or communication link or a mobile telephone network (MTN) communication channel or communication link. Consequently, devices (e.g., the monitoring device 102 and the computing device 106) that communicate via the primary monitoring communication mode 112 instead of the secondary monitoring communication mode 116 may (i) experience longer battery life, (ii) include higher fidelity, (iii) be less prone to disconnect, (iv) minimize latency, etc.

In various embodiments, while operating in the primary monitoring communication mode 112 to implement monitoring functionality (e.g., receiving video of a baby sleeping in a crib), the computing device 106 may also be configured to simultaneously communicate with remote devices via one or more network(s) 120 to perform functionality other than the monitoring functionality. In some embodiments, the remote devices may include one or more servers or other computing devices that operate within a network service (e.g., a cloud service). The network(s) 120 may include the Internet, a Mobile Telephone Network (MTN) or other various communication technologies.

Figure 2:
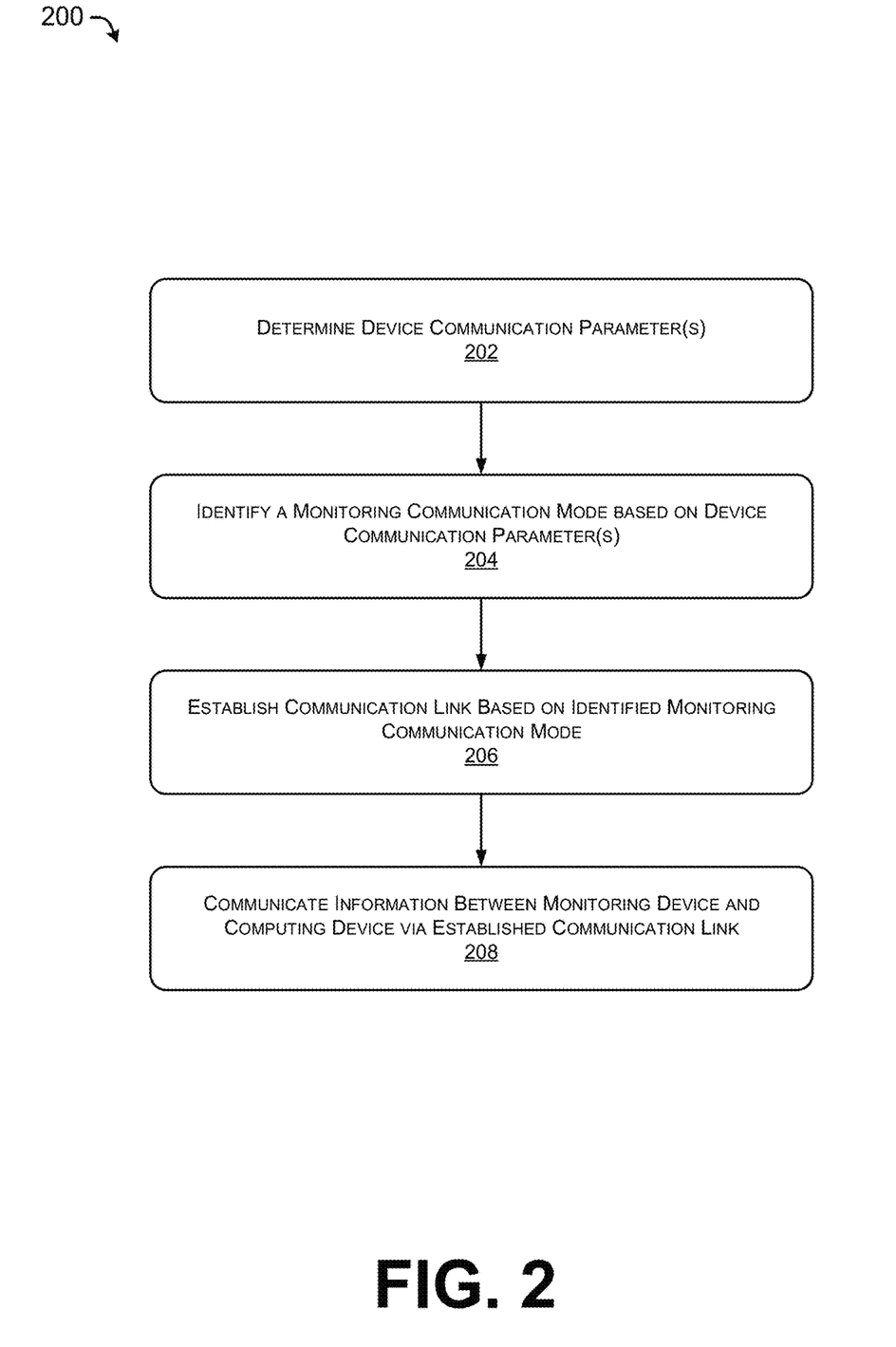
FIG. 2 illustrates an example process that determines in which one of multiple monitoring communication modes to operate a device.
Figure 3:
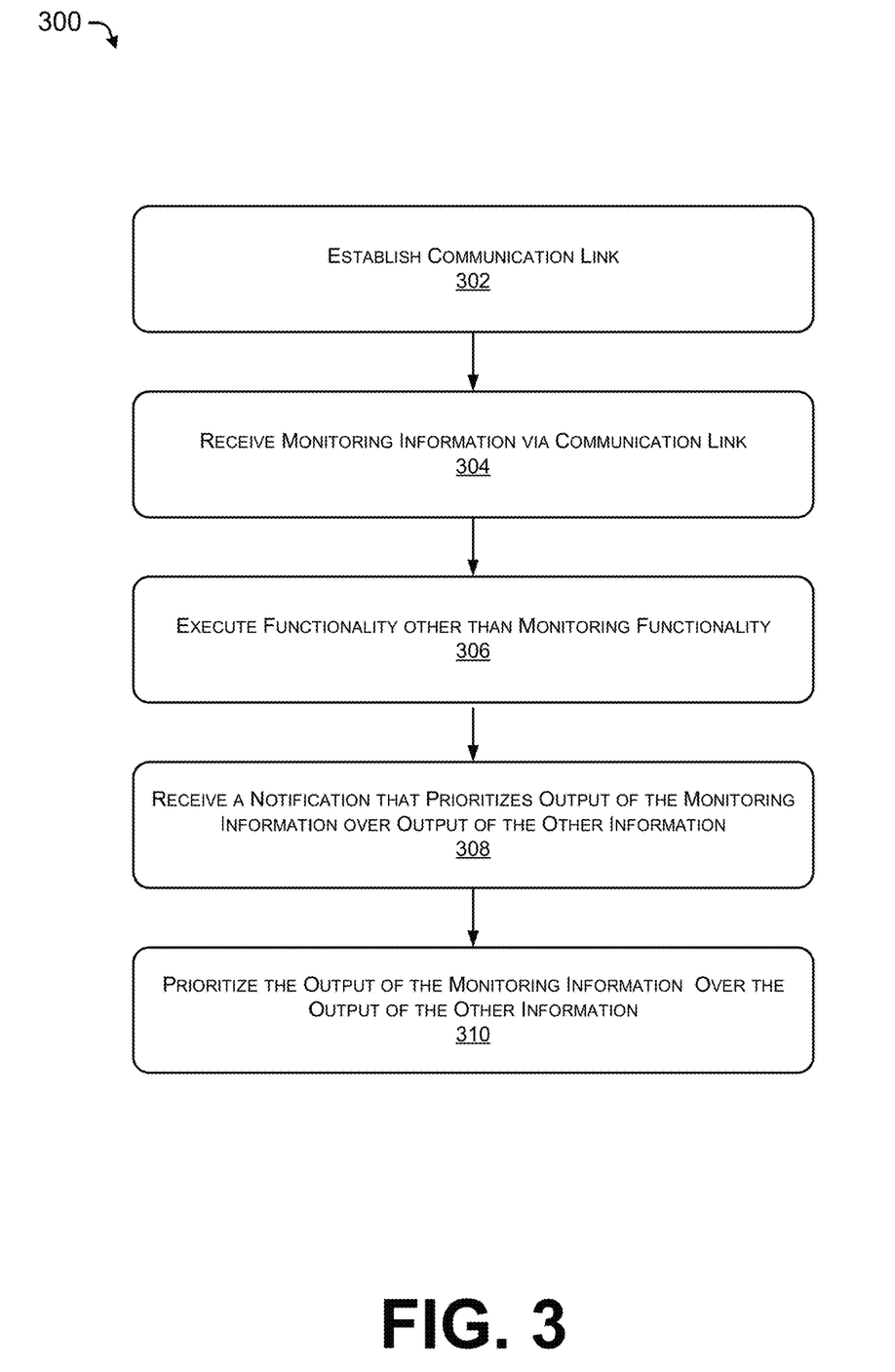
FIG. 3 illustrates an example process that prioritizes monitoring functionality of a device over other device functionality.
Figure 4:
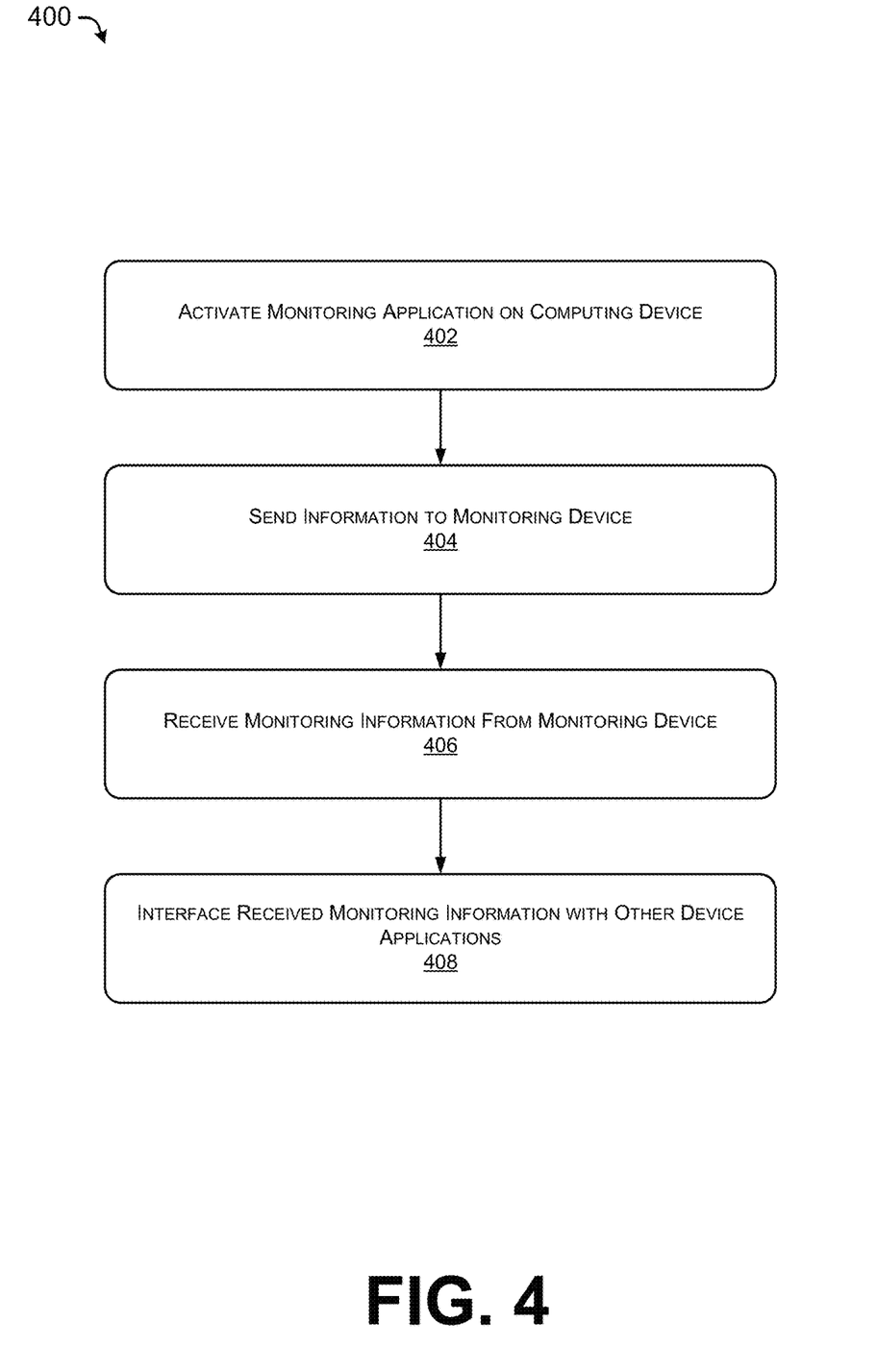
FIG. 4 illustrates an example process that interfaces received monitoring information with other applications on a device (e.g., via one or more application program interfaces).

FIGS. 2, 3 and/or 4 illustrate example processes depicted as logical flow graphs, which represent a sequence of operations that can be implemented in hardware, software, firmware, or a combination thereof. In the context of software, the operations represent computer-executable instructions that, when executed by one or more processors, configure a computing device to perform the recited operations. Generally, computer-executable instructions include routines, programs, objects, components, data structures, and the like that configure a computing device to perform particular functions or implement particular abstract data types. In some embodiments, any or all of the operations may be implemented in whole or in part by hardware (e.g., as an ASIC, a specialized processing unit, etc.) to execute the described functions. In some instances, the functions and/or modules are implemented as part of an operating system. In other instances, the functions and/or modules are implemented as part of a device driver (e.g., a driver for a touch surface), firmware, and so on. The order in which the operations are described is not intended to be construed as a limitation, and any number of the described operations can be combined in any order and/or in parallel to implement the processes. The example operations in FIGS. 2, 3 and/or 4 may be described with reference to the components and/or elements illustrated in FIG. 1.

FIG. 2 illustrates an example process 200 that determines in which one of multiple monitoring communication modes to operate devices (e.g., the monitoring device 102 and the computing device 106).

At 202, the monitoring application 108 determines device communication parameter(s) for the computing device 106 and/or the monitoring device 102. For example, the monitoring application 108 may determine whether the computing device 106 is within a communication range (e.g., twenty meters, fifty meters, seventy meters, one hundred meters and so forth) of the monitoring device 102 so that the primary monitoring communication mode 112 can be used (e.g., high quality video, less drain on battery power of devices, etc.). In some instances, the communication range may completely encompass a residential dwelling (e.g., a house) where a baby and the parents live and/or may be defined by RF communication limits. Thus, the monitoring application 108 may evaluate the strength of a signal (e.g., RF communication channel) to determine a device communication parameter. If the computing device 106 is outside the communication range (e.g., outside a defined area or not receiving a signal of sufficient strength), then the secondary monitoring communication mode 116 may be used for monitoring purposes. In various embodiments, the monitoring application 108 determines the device communication parameters in response to an instruction received at the computing device 106 from a monitoring person (e.g., a parent). In alternative embodiments, the monitoring application 108 determines the device communication parameters automatically (e.g., periodic schedule, in response to the computing device 106 transitioning from in range 114 to out of range 118, etc.). The device communication parameters may be determined using any one of a variety of device positioning or location techniques (e.g., global positioning systems) or signal strength.

At 204, the monitoring application 108 identifies a monitoring communication mode in which to operate the monitoring device 102 and the computing device 106 based on the device communication parameters determined in 202. For example, if the computing device 106 is within a particular communication range of the monitoring device 102, the monitoring application 108 may configure the computing device 106 to communicate with the monitoring device 106 via the primary monitoring communication mode 112. If the computing device 106 is outside the particular communication range of the monitoring device 102 (or moves outside the particular communication range of the monitoring device 102), then the monitoring application 108 may configure the computing device 106 to communicate with the monitoring device 106 via the secondary monitoring communication mode 116.

At 206, the monitoring application 108 establishes a communication link or a communication channel based on the identified monitoring communication mode (e.g., the primary monitoring communication mode 112 or the secondary monitoring communication mode 116).

At 208, the monitoring application 108 communicates with the monitoring device 102 via the established communication link (e.g., receives information from, and/or transmits information to, the monitoring device 102).

FIG. 3 illustrates an example process 300 that prioritizes monitoring functionality of a device (e.g., the computing device 106) over other device functionality.

At 302, the monitoring application 108 establishes a communication link or a communication channel with the monitoring device 106 (e.g., in the primary monitoring communication mode 112 or the secondary monitoring communication mode 116).

At 304, the monitoring application 108 receives monitoring information via the established link. For example, the monitoring information may include, but is not limited to, streaming video (e.g., of a crib where a baby sleeps), temperature information (e.g., of a room in a house where the crib is located), and so forth. In various embodiments, the monitoring information may be communicated from the monitoring device 102 to the computing device 106 continuously or in accordance with a periodic schedule (e.g., every five seconds, ten seconds, thirty seconds, one minute, ten minutes, etc.).

At 306, the computing device 106 may execute functionality (e.g., the other application(s) 110) other than the monitoring functionality. For instance, a display or output of a monitoring interface that allows a parent to view a sleeping baby (e.g., the streamed video) and/or the temperature of a room, may no longer be the main focus on the display screen of the computing device 106 (e.g., the streaming video may be minimized or run as a background process or a standby mode). Instead, a large portion of the display screen of the computing device 106 may be used to output information related to web browsing, gaming, social media applications, streaming music, etc. (e.g., the functionality other than the monitoring functionality). In some embodiments, the execution of the functionality other than the monitoring functionality may use a network connection established via the one or more network(s) (e.g., an Internet connection, a Wi-Fi connection, an MTN connection, etc.). Thus, in a scenario where the computing device 106 is within the predefined range of the monitoring device 102 and communicating via the primary monitoring communication mode 112, the computing device 106 may be configured to receive the monitoring information via an RF communication channel (e.g., 2.4 GHz) while permitting the user (e.g., a parent) of the computing device 106 to simultaneously browse the Internet via a different communication channel (e.g., a Wi-Fi connection).

At 308, the monitoring application 108 receives a notification, e.g., from the monitoring device 102, that prioritizes the output of the monitoring information at the computing device 106 over other information related to the functionality other than the monitoring functionality. That is, the monitoring device 102 may generate and communicate the notification to alert a parent of the computing device 106 of a potential issue with the baby. For example, the monitoring device 102 may generate and communicate the notification to alert the parent when one or more sensors detect a threshold amount of motion (e.g., the baby sits up or rolls over, etc.). In another example, the monitoring device 102 may generate and communicate the notification to alert the parent when one or more sensors detect a threshold amount of noise (e.g., the baby begins to cry or talk compared to soft sounds associated with breathing). In yet another example, the monitoring device 102 may generate and communicate the notification to alert the parent when one or more sensors detect that the temperature of the room has passed a minimum threshold temperature (e.g., sixty-five degrees Fahrenheit, seventy-two degrees Fahrenheit, etc.) or a maximum threshold temperature (e.g., eighty degrees Fahrenheit, eighty-four degrees Fahrenheit, etc.).

In some embodiments, the computing device 106 may receive the sensed information from the monitoring device 102 and the computing device 106 may analyze the information to determine whether a notification is to be output to alert the parent (e.g., the computing device 106 determines if the sensed information meets or exceeds the thresholds discussed above).

Accordingly, the computing device 106 is configured to receive the notification from the monitoring device 102 via the established communication link (e.g., an RF communication channel or a Wi-Fi communication channel). The monitoring device 102 may be configured to send a notification to the computing device 106 in response to detecting a crying baby, detecting potentially dangerous baby movement, detecting a person other than the monitoring parent (e.g., a stranger, an intruder, a nanny, a spouse) entering the room and/or approaching the baby. In some instances, the monitoring device 102 may be configured to perform recognition techniques (e.g., facial recognition, height/weight recognition) to identify the person and determine whether the person is a known person who is supposed to be checking on the baby (e.g., a nanny or a spouse) or an unknown dangerous person (e.g., a stranger or an intruder).

At 310, the monitoring application 108 prioritizes the output of the monitoring information over the output of the other information related to the functionality other than the monitoring functionality. For example, since viewing streaming video of a baby moving and/or crying is typically more important than other functionality (e.g., checking social media posts, shopping online, etc.), the monitoring application 108 may provide a notification informing the parent to prioritize, or focus, on the monitoring information. Or the monitoring application 108 may automatically maximize, or bring to the forefront, a monitoring interface that displays the monitoring information and allows the parent to view the streamed video, to hear the audio/noise in the room, to view the temperature of the room, and so forth.

FIG. 4 illustrates an example process 400 that interfaces received monitoring information with other applications on a device (e.g., via one or more application program interfaces APIs).

At 402, the computing device 106 activates the monitoring application 108. For example, the computing device 106 may receive an instruction to configure and operate the monitoring application 108. The instruction may be received from a user at the computing device 106 (e.g., a user selection of the monitoring application 108) or the instruction may be received from another device such as the monitoring device 102 (e.g., the parent turns on the monitoring device 102 which may then automatically send the instruction to the computing device).

At 404, the monitoring application 108 may send information from the computing device 106 to the monitoring device 102. For example, a parent operating the computing device 106 may select music (e.g., lullabies) stored on the computing device or to be downloaded to the computing device 106 via networks 120, and the monitoring application may send the music to the monitoring device 102 to be output (e.g., play the music to help the baby fall asleep). In another example, the information may indicate a type of monitoring information the parent wishes to receive at the computing device 106 (e.g., one or more of streaming video, temperature of room, audio in room, a notification when someone enters the room, etc.).

At 406, the monitoring application 108 receives the monitoring information from the monitoring device 102. For instance, the monitoring device 102 may send the monitoring information to the computing device 106 for a predetermined period of time (e.g., one hour, two hour, etc.) or until an instruction from a parent indicating to stop the monitoring is received. In some implementations, the monitoring information is stored at the computing device 106.

At 408, the monitoring application 108 is configured to provide access (e.g., interface) to the received monitoring information. For example, other device applications 110 (e.g., social media applications, other baby applications, etc.) may access, evaluate and/or process the monitoring information received (e.g., imagery, sounds, temperature, etc.). For example, a particular application may determine and/or identify a baby photo or a baby video of the day to place in calendar or post to a social media timeline. As part of the photo or video identification process, the monitoring device 102 and/or the computing device 106 may be configured to recognize a person in a photo or video with a baby (e.g., facial recognition techniques). Consequently, baby photos with a mother and baby photos with a father can be sorted, for example.

In various embodiments, the monitoring application 108 may be configured to upload streaming video from the monitoring device 102 to a ME server.

As discussed above, the computing device 106 may be configured (e.g., pre-loaded) with a variety of applications directed to parenting. Thus, users of the computing device 106 are provided with a complete and dedicated parenting experience that is convenient and easy to use. The following describes example applications executable on the computing device 106 that are directed to parenting. In some implementations, the applications may use monitoring information received from the monitoring device 102.

The following describes example applications executable on the computing device 106 that may use monitoring information received from the monitoring device 102. In various embodiments, the apps described below may be individual apps on the computing device 106. In alternative embodiments, two or more of the apps described below may be part of a single app on the computing device 106.

A baby bonding app allows parents to store and update, over time, content (e.g., photos and videos) related to a baby.

A baby calendar app allows parent to identify and/or capture "a baby photo or video of the day" or a "baby sound of the day" (e.g., based on the monitoring information). For example, the baby calendar app may allow a parent to review a set of photos captured in a day (e.g., one hundred photos) and populate a baby calendar with a photo from each day. Moreover, the baby calendar app may allow a parent to add their own notes or captions to a photo or a video (e.g., "today Joe started rolling over in his bed.").

A baby milestone tracker app is configured to log or record growth of the baby (e.g., increases in height or weight) or particular events (e.g., date baby begins crawling, date baby begins walking, date potty training commences, etc.). Accordingly, the parents can use the logged information to generate a growth chart with pictures and/or an event timeline.

A baby stories app that allows parents to extract precious moments from a timeline of photos, videos and events, and build a story based on the moments.

A schedule/activity tracker app allows parents to log or record tasks associated with a baby (e.g., diaper changes, feedings, naps, pooping, etc.).

A baby cry translator and analyzer app allows parents to determine an intensity of a baby crying app and determine what may be causing the baby to cry.

A parent support app provides parents with a forum to chat with each other and share photos and videos of a baby. In some implementations, the parent support app may interface with popular social media applications.

A baby e-health app connects the computing device 106 to doctors and/or specific medical information for the baby or general baby medical information.

A task organizer app allows parents to log or record information associated with a baby (e.g., a number of clean diapers at the house, an amount of milk left to feed the baby). The task organizer app may be configured to remind parents to buy products (e.g., diapers, food, milk, etc.) when the stock is low. The task organizer app may also remind parents the time to feed the baby, change diapers, check baby health, etc.

A smart cabinet app locks cabinets, e.g., in the house, in response to a notification indicating a baby is in the house and/or free to move (e.g., walk, crawl) in an area where the cabinets are located.

Conclusion

Although the present disclosure may use language that is specific to structural features and/or methodological acts, the invention is not limited to the specific features or acts described herein. Rather, the specific features and acts are disclosed as illustrative forms of implementing the invention. Moreover, provided herein are three appendices (e.g., Appendix A, Appendix B, Appendix C) that provide example embodiments of the techniques and systems discussed above.

What is claimed is:

1. One or more non-transitory computer-readable media storing instructions that, when executed by one or more processors, configure a computing device to perform operations comprising:
    establishing a communication link with a monitoring device;
    receiving monitoring information associated with a baby or associated with an area in which the baby is located from the monitoring device via the communication link;
    receiving a notification from the monitoring device via the communication link, the notification being associated with the monitoring device detecting a threshold amount of monitoring information;
    in response to receiving the notification, prioritizing output of at least part of the monitoring information at the computing device over other information currently being output at the computing device, wherein a monitoring interface that displays the monitoring information is automatically maximized or brought to forefront to allow a user to view a streamed video, to hear audio/noise in an area, and/or to view temperature of the area;
    causing the at least part of the monitoring information to be output at the computing device;
    simultaneously performing one or more functionalities configured on the computing device in addition to continually receiving the monitoring information associated with the baby or associated with the area in which the baby is located;
    wherein the monitoring device is configured to communicate with the computing device via both a primary monitoring communication mode and a secondary monitoring communication mode concurrently.

2. The one or more non-transitory computer-readable media of claim 1, wherein the communication link via which the monitoring information is received is a first communication link and the computing device establishes a second communication link to simultaneously receive the other information currently being output at the computing device.

3. The one or more non-transitory computer-readable media of claim 2, wherein the first communication link comprises a radio frequency RF communication link and the second communication link comprises at least one of a Wi-Fi communication link or a mobile telephone network MTN communication link.

4. The one or more non-transitory computer-readable media of claim 1, wherein the threshold amount of monitoring information comprises a threshold amount of motion of a monitored subject.

5. The one or more non-transitory computer-readable media of claim 1, wherein the threshold amount of monitoring information comprises a threshold amount of noise of a monitored subject.

6. The one or more non-transitory computer-readable media of claim 1, wherein the monitoring device comprises a camera configured with one or more sensors to capture audio and visual information of a monitored subject.

7. A method, comprising:
    establishing a communication link with a monitoring device;
    receiving monitoring information associated with a baby or associated with an area in which the baby is located from the monitoring device via the communication link;
    receiving a notification from the monitoring device via the communication link, the notification being associated with the monitoring device detecting a threshold amount of monitoring information;
    in response to receiving the notification, prioritizing output of at least part of the monitoring information at a computing device over other information currently being output at the computing device, wherein a monitoring interface that displays the monitoring information is automatically maximized or brought to forefront to allow a user to view a streamed video, to hear audio/noise in an area, and/or to view temperature of the area;
    causing the at least part of the monitoring information to be output at the computing device;
    simultaneously performing one or more functionalities configured on the computing device in addition to continually receiving the monitoring information associated with the baby or associated with the area in which the baby is located;

wherein the monitoring device is configured to communicate with the computing device via both a primary monitoring communication mode and a secondary monitoring communication mode concurrently.

8. The method of claim 7, wherein the communication link via which the monitoring information is received is a first communication link and the computing device establishes a second communication link to simultaneously receive the other information currently being output at the computing device.

9. The method of claim 8, wherein the first communication link comprises a radio frequency RF communication link and the second communication link comprises at least one of a Wi-Fi communication link or a mobile telephone network MTN communication link.

10. The method of claim 7, wherein the threshold amount of monitoring information comprises a threshold amount of motion of a monitored subject.

11. The method of claim 7, wherein the threshold amount of monitoring information comprises a threshold amount of noise of a monitored subject.

12. The method of claim 7, wherein the monitoring device comprises a camera configured with one or more sensors to capture audio and visual information of a monitored subject.

13. A method comprising:
determining, by one or more processors, whether a computing device is within a particular range to communicate with a monitoring device;
if the computing device is within the particular range, configuring the computing device to communicate with the monitoring device via a primary monitoring communication mode;
if the computing device is outside the particular range, configuring the computing device to communicate with the monitoring device via a secondary monitoring communication mode;
receiving, at the computing device and from the monitoring device via the primary monitoring communication mode or the secondary monitoring communication mode, a notification including monitoring information associated with a baby or associated with an area in which the baby is located;
prioritizing an output of the monitoring information associated with the baby or associated with the area in which the baby is located on the computing device over another output of one or more functionalities of the computing device by generating and communicating an alert notification informing a user to focus on the monitoring information over the one or more functionalities in response to the monitoring information indicating more than a threshold amount of motion, more than a threshold amount of noise, more or less than a threshold temperature, or presence of a person other than a designated person, wherein the output of the monitoring information automatically maximizes or brings to a forefront on the computing device; and
simultaneously performing the one or more functionalities configured on the computing device in addition to continually receiving the monitoring information associated with the baby or associated with the area in which the baby is located;
wherein the monitoring device is configured to communicate with the computing device via both the primary monitoring communication mode and the secondary monitoring communication modes concurrently.

14. The method of claim 13, wherein the primary monitoring communication mode communicates the monitoring information via a radio frequency RF communication channel.

15. The method of claim 13, wherein the secondary monitoring communication mode communicates the monitoring information via at least one of a Wi-Fi communication channel or a mobile telephone network MTN communication channel.

16. The method of claim 13, wherein the particular range encompasses a residential dwelling.

17. The method of claim 13, further comprising using device positioning or device location techniques to determine whether the computing device is within the particular range to communicate with the monitoring device.

18. The method of claim 13, further comprising evaluating a strength of a signal to determine whether the computing device is within the particular range to communicate with the monitoring device.

19. The method of claim 13, wherein the monitoring device comprises a camera configured with one or more sensors to capture video of the baby.

20. The method of claim 13, wherein the monitoring device is configured to determine, based on audio and visual information, an identity of the person in the area in which the baby is located.

* * * * *